United States Patent
Ishizuka

(10) Patent No.: US 6,565,506 B2
(45) Date of Patent: May 20, 2003

(54) ENDOSCOPE

(75) Inventor: Tatsuya Ishizuka, Hachioji (JP)

(73) Assignee: Olympus Optical Co., Ltd., Tokyo (JP)

( * ) Notice: Subject to any disclaimer, the term of this patent is extended or adjusted under 35 U.S.C. 154(b) by 0 days.

(21) Appl. No.: 09/909,275

(22) Filed: Jul. 19, 2001

(65) Prior Publication Data

US 2002/0019581 A1 Feb. 14, 2002

(30) Foreign Application Priority Data

Jul. 28, 2000 (JP) ........................................ 2000-229509

(51) Int. Cl.$^7$ ................................................ A61B 1/00
(52) U.S. Cl. .................... 600/139; 600/140; 600/133
(58) Field of Search .............................. 600/134, 140, 600/133, 144, 153

(56) References Cited

U.S. PATENT DOCUMENTS

| | | | | |
|---|---|---|---|---|
| 4,690,175 A | * | 9/1987 | Ouchi et al. | 138/131 |
| 4,753,222 A | * | 6/1988 | Morishita | 600/140 |
| 4,899,787 A | * | 2/1990 | Ouchi et al. | 138/131 |
| 4,977,887 A | * | 12/1990 | Gouda | 600/140 |
| 5,448,988 A | * | 9/1995 | Watanabe | 138/118 |
| 5,885,207 A | * | 3/1999 | Iwasaka | 600/139 |
| 5,885,208 A | * | 3/1999 | Moriyama | 600/144 |

FOREIGN PATENT DOCUMENTS

JP      2-10802      1/1990

* cited by examiner

*Primary Examiner*—Linda C. M. Dvorak
*Assistant Examiner*—Kenneth G Schopfer
(74) *Attorney, Agent, or Firm*—Scully, Scott Murphy & Presser

(57) ABSTRACT

An elongated built-in component formed with a hollow resin tube is passed through a flexible tube that is an integral part of a soft insertion member of an endoscope. Assuming that a critical radius of curvature the flexible tube exhibits after completion of sterilization with high-temperature high-pressure steam is Rj, and a critical radius of curvature the elongated built-in component exhibits after completion of the sterilization is Rn, the condition of Rj≧Rn is met. Unless the flexible tube is bent to exhibit so small a radius of curvature as to cause the flexible tube to buckle, the built-in component will not buckle.

27 Claims, 8 Drawing Sheets

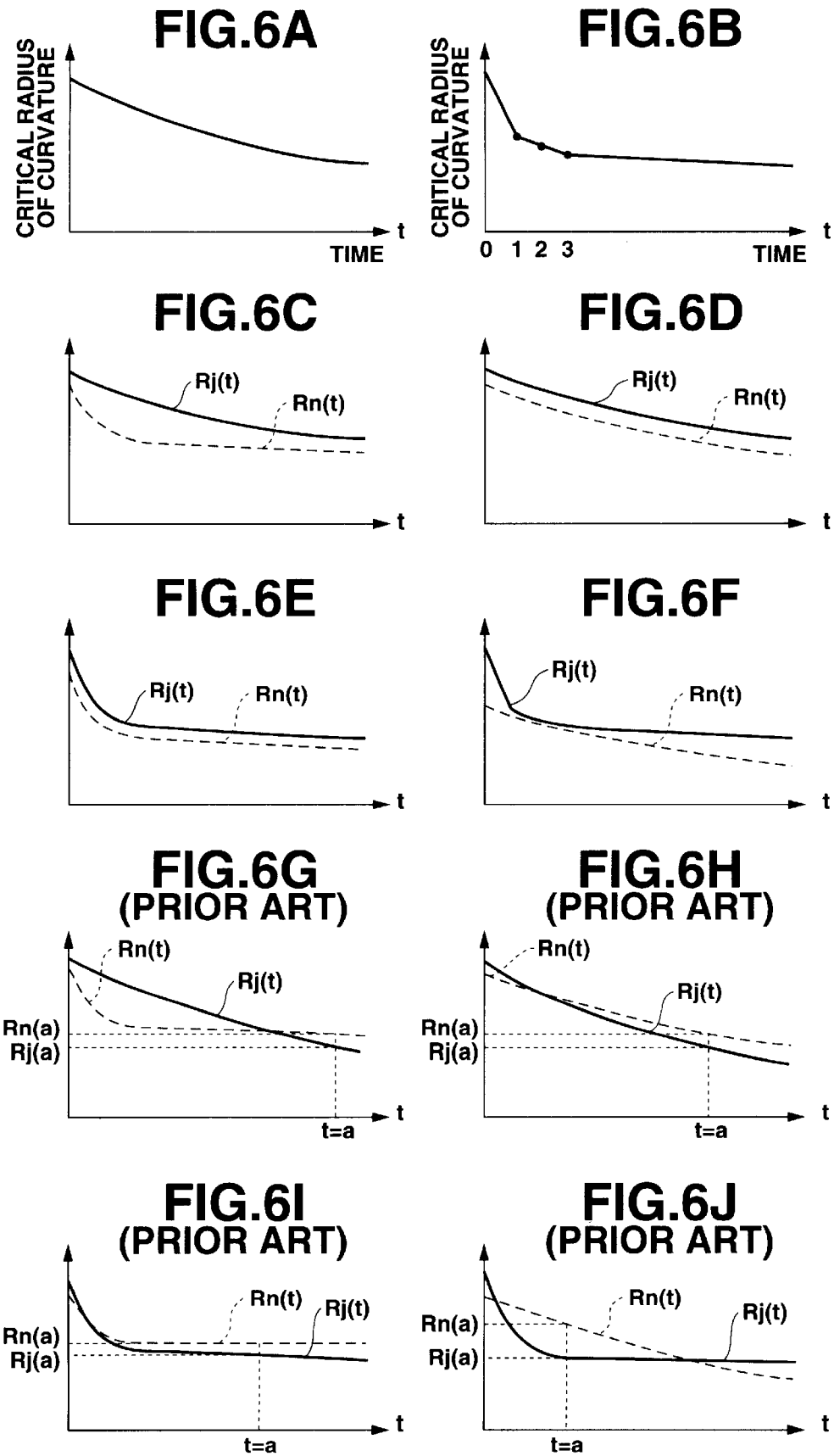

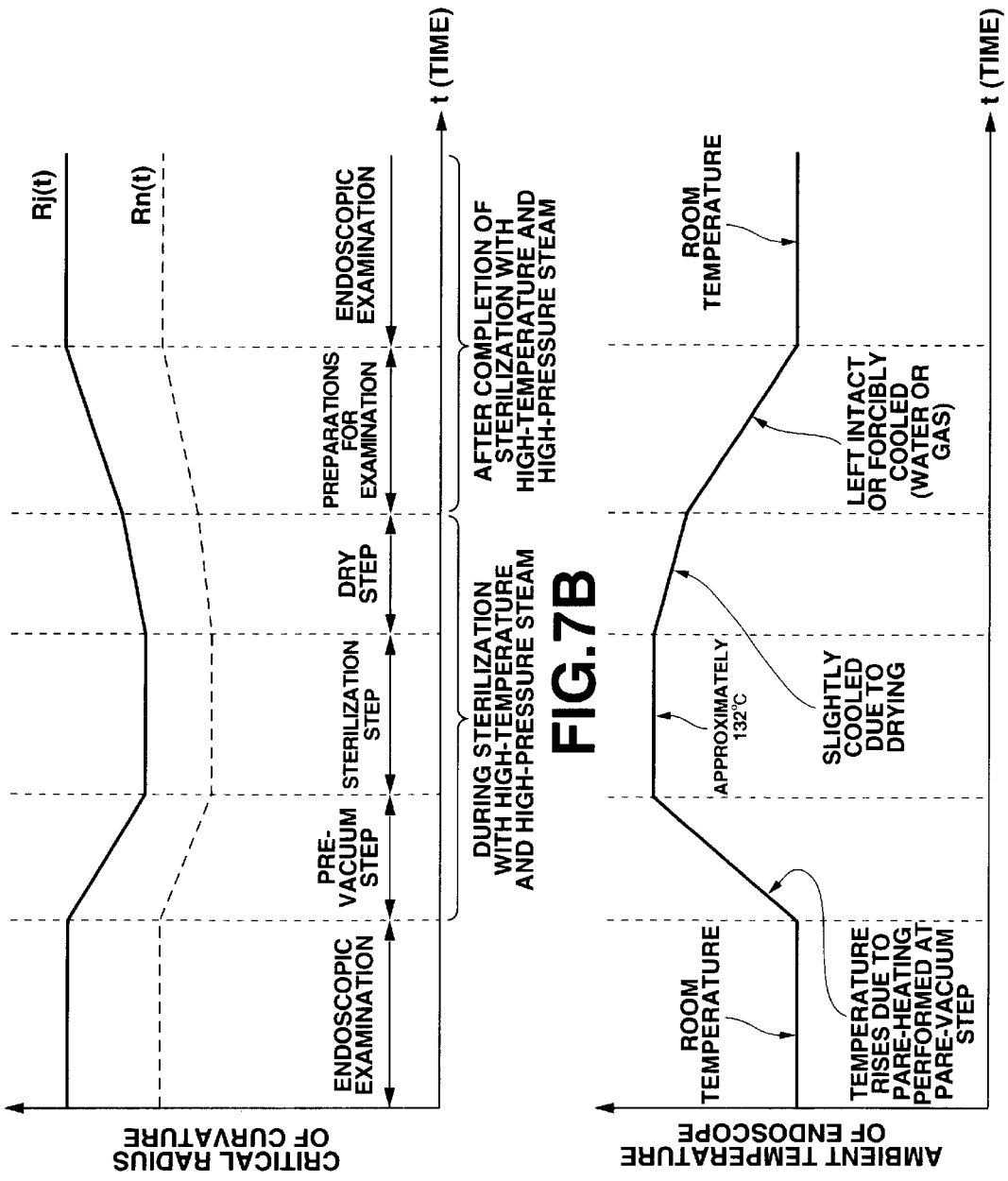

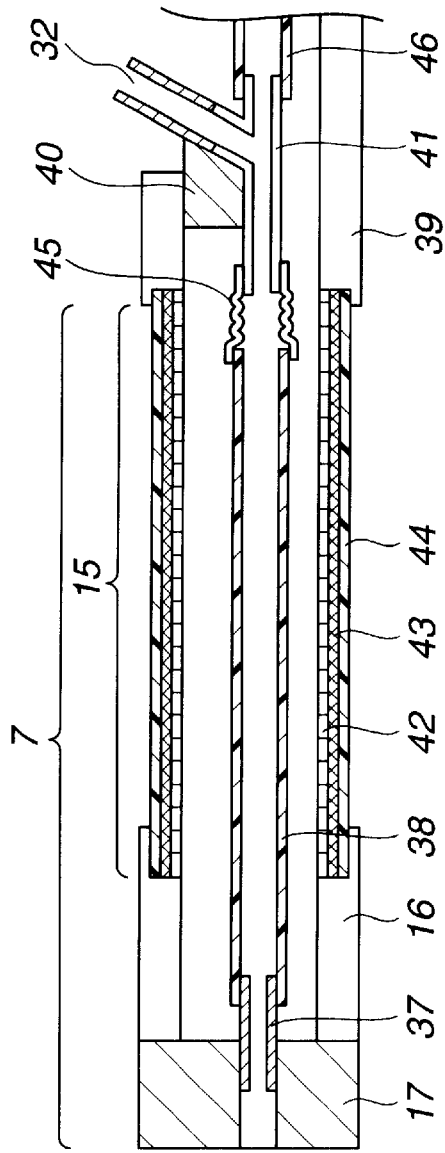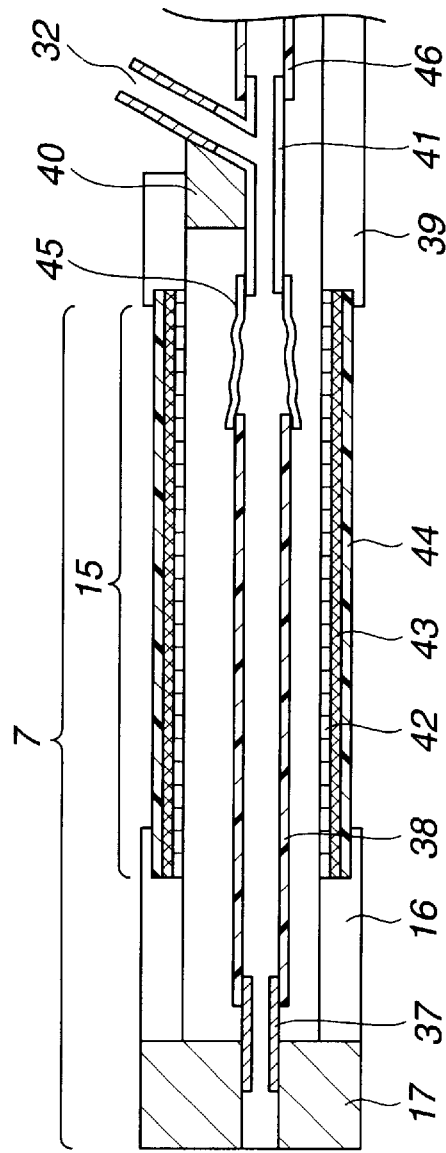

ENDOSCOPE

This application claims benefit of Japanese Application No. 2000-229509 filed in Japan on Jul. 28, 2000, the contents of which are incorporated by this reference.

BACKGROUND OF THE INVENTION

1. Field of the Invention

The present invention relates to an endoscope having a soft insertion member and capable of being sterilized with high-temperature high-pressure steam.

2. Description of the Related Art

In recent years, endoscopes have been widely employed in the field of medicine and the field of industry alike. The related arts of the endoscopes include an art disclosed in Japanese Unexamined Utility Model Publication No. 2-10802.

According to the Japanese Unexamined Utility Model Publication No. 2-10802, the flexibility of a flexible tube is changed at at least one point in an axial direction thereof so that it will be different between the back-and-forth portions of the flexible tube relative to the point. The flexibility in axial directions of at least one built-in component is changed in the middle of the built-in component. The point on the built-in component at which the flexibility of the built-in component is changed is located near the point on the flexible tube at which the flexibility of the flexible tube is changed.

In the foregoing structure, supposing the endoscope can be sterilized with high-temperature high-pressure steam, after sterilization is completed, the flexibilities of the flexible tube and built-in components vary. Consequently, the radii of curvature of the flexible tube and built-in components may change.

For example, the radius of curvature the built-in component exhibits after completion of sterilization with high-temperature high-pressure steam is larger than the radius of curvature the flexible tube exhibits after completion of the sterilization. In this case, when the flexible tube is bent, although the flexible tube is not buckled, the built-in component incorporated in the flexible tube may be buckled, which may cause certain inconvenience.

SUMMARY OF THE INVENTION

Accordingly, an object of the present invention is to provide an endoscope in which even after completion of sterilization with high-temperature high-pressure steam, unless a flexible tube buckles, a built-in component will not buckle.

Another object of the present invention is to provide a durable endoscope that is repeatedly usable for endoscopic examination.

An endoscope has a soft insertion member that includes a flexible tube. The flexible tube is flexible and has a flexible elongated built-in component incorporated therein. The endoscope withstands sterilization with high-temperature high-pressure steam during which an endoscope is sterilized while being exposed to high-temperature high-pressure steam.

A critical radius of curvature Rn exhibits the elongated built-in component after completion of sterilization with high-temperature high-pressure steam is equal to or smaller than a critical radius of curvature Rj the flexible tube exhibits after completion of the sterilization, that is, the condition of $Rn \leq Rj$ is met. Herein, after completion of sterilization with high-temperature high-pressure steam, if the elongated built-in component is bent to exhibit a radius of curvature equal to or smaller than the critical radius of curvature Rn, the elongated built-in component is buckled. After completion of the sterilization, if the flexible tube is bent to exhibit a radius of curvature equal to or smaller than the critical radius of curvature Rj, the flexible tube is buckled. Consequently, unless the flexible tube is bent to exhibit a radius of curvature equal to or smaller than the critical radius of curvature Rj that causes the flexible tube to buckle, the elongated built-in component will not buckle.

BRIEF DESCRIPTION OF THE DRAWINGS

FIG. 1 to FIG. 4B are concerned with a first embodiment of the present invention;

FIG. 2 is a longitudinal sectional view showing the structure of a flexible tube of an endosocope;

FIG. 3 is a longitudinal sectional view showing the structure of the elongated built-in component;

FIG. 4A and FIG. 4B show the critical radii of curvature of the flexible tube and an elongated built-in component respectively;

FIG. 6A to FIG. 7B are concerned with a fifth embodiment of the present invention;

FIG. 6A and FIG. 6B schematically show the time-passing changes in the critical radii of curvature of a flexible tube and an elongated built-in component employed in the fifth embodiment;

FIG. 6C to FIG. 6F concretely show the time-passing changes in the critical radii of curvature of the flexible tube and elongated built-in component;

FIG. 6G to FIG. 6J show, for comparison, the time-passing changes in the critical radii of curvature of a flexible tube and an elongated built-in component employed in a related art;

FIG. 7A shows the changes in the critical radii of curvature of a flexible tube and an elongated built-in component from the start of an endoscopic examination through sterilization with high-temperature high-pressure steam to the start of the next endoscopic examination;

FIG. 7B shows the change in the ambient temperature of the endoscope;

FIG. 10A is a cross-sectional view showing the structure of a flexible tube employed in the tenth embodiment;

FIG. 10B is a cross-sectional view showing the structure of a flexible tube employed in a related art for comparison with the flexible tube shown in FIG. 10A;

FIG. 12A and FIG. 12B are longitudinal sectional views showing the states of a major portion of an insertion member attained before start of sterilization with high-temperature high-pressure steam and after completion thereof.

DESCRIPTION OF THE PREFERRED EMBODIMENTS (First Embodiment)

Referring to FIG. 1 to FIG. 4B, a first embodiment of the present invention will be described below.

Figure 1:
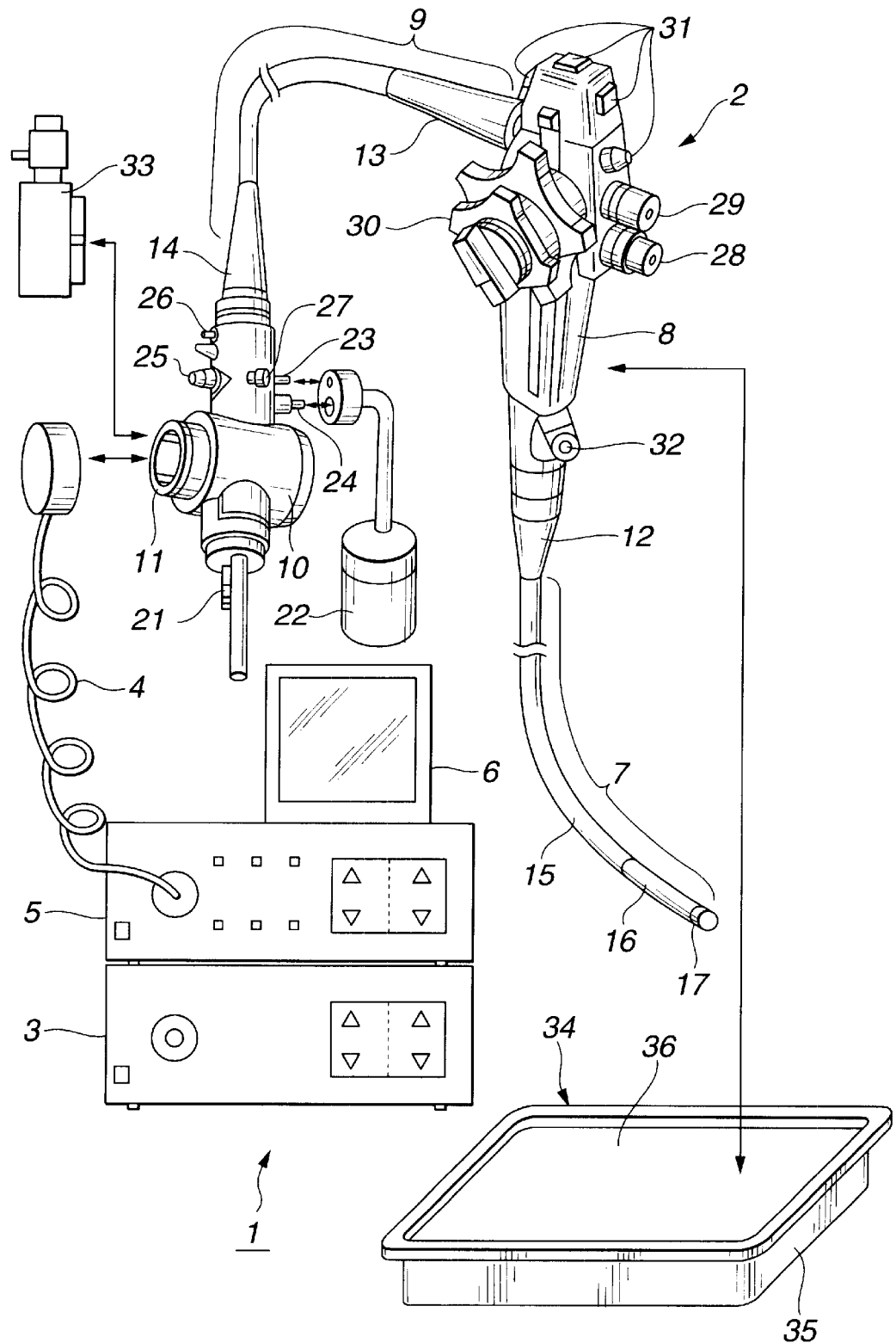

As shown in FIG. 1, an endoscope system 1 consists mainly of an endoscope 2 in accordance with the first embodiment, a light source apparatus 3, a video processor 5, and a monitor 6. The endoscope 2 has an imaging means. The light source apparatus 3 is connected to the endoscope 2 so that it can be disconnected freely, and supplies illumination light to a light guide lying through the endoscope 2. The video processor 5 connected to the endoscope 2 over a signal cable 4 controls the imaging means incorporated in the endoscope 2, and processes a signal produced by the imaging means. An object image is displayed on the monitor 6 according to a video signal produced by the video processor 5.

The endoscope 2 is structured so that when used for observation or treatment, after cleaned, the endoscope 2 can be sterilized with high-temperature high-pressure steam.

The endoscope 2 consists mainly of an elongated insertion member 7, a control section 8, a linkage cord 9, a connector unit 10, and an electric connector 11. The insertion member 7 is flexible (soft). The control section 8 is coupled to the proximal end of the insertion member 7. The linkage cord 9 that is flexible is extended from the lateral part of the control section 8. The connector unit 10 is fixed to an end of the linkage cord 9 and connected to the light source apparatus 3 so that it can be disconnected freely. The electric connector 11 is formed on the lateral part of the connector unit 10. A connector fixed to an end of the signal cable 4 coupled to the video processor 5 is mated with the electric connector 11 so that the connector can be freely separated from the electric connector 11.

An air vent hole that is not shown is formed in the electric connector 11. The air vent hole links the interior of the endoscope 2 and the exterior thereof.

An anti-breakage member 12 at the insertion member side formed with an elastic member is fixed to the proximal end of the insertion member 7 in order to prevent abrupt bending of a joint between the insertion member 7 and control section 8. Likewise, an anti-breakage member 13 at the control section side analogous to the anti-breakage member 12 at the insertion member side is mounted on a joint between the control section 8 and linkage cord 9. An anti-breakage member 14 at the connector unit side analogous to the anti-breakage member 12 at the insertion member side is mounted on a joint between the linkage cord 9 and connector unit 10.

The insertion member 7 consists mainly of a flexible tube 15, a bending section 16, and a distal part 17. The flexible tube 15 is flexible and soft. The bending section 16 is located distally to the flexible tube 15 and can be bent while being remotely controlled at the control section 8. The distal part 17 is located distally to the bending section 16, and an observation optical system and an illumination optical system that are not shown are incorporated in the distal part 17.

An aeration/perfusion nozzle and a suction port are formed in the distal part 17. When aeration or perfusion is instructed, cleaning fluid or gas is jetted out to an optical member located outside the observation optical system, which is not shown, through the aeration/perfusion nozzle. The suction port is an opening of a therapeutic instrument passage channel that runs through the insertion member 7. A therapeutic instrument is inserted through the suction port, or fluid is sucked from a body cavity through the suction port. Moreover, a fluid port through which fluid is jetted out opens onto an object of observation.

The connector unit 10 has an air supply base 21, a water supply tank pressurization base 23, and a fluid supply base 24. The air supply base 21 is connected to an air source, which is not shown, incorporated in the light source apparatus 3 so that it can be disconnected freely. The water supply tank pressurization base 23 and fluid supply base 24 are connected to a water supply tank 22, which is a fluid source, so that they can be disconnected freely.

Moreover, the connector unit 10 has a suction base 25 that is connected to a sucking device which is not shown. The sucking device sucks fluid through the suction port. In addition, the connector unit 10 has an injection base 26 that is connected to a water supply means which is not shown. The water supply means supplies water through the fluid supply port.

Moreover, the connector unit 10 has a ground base 27 through which high-frequency leakage current is fed back to a diathermy device if the leakage current develops in the endoscope during diathermy.

The control unit 8 has an aeration/perfusion button 28, a suction button 29, an angling knob 30, a plurality of remote-control switches 31, and a therapeutic instrument insertion port 32. The aeration/perfusion button 28 is pressed in order to instruct aeration or perfusion. The suction button 29 is pressed in order to instruct suction. The angling knob 30 is manipulated to bend the bending section 16. The plurality of remote-control switches 31 is used to remotely control the video processor 5. The therapeutic instrument insertion port 32 is an opening that opens onto the therapeutic instrument channel.

Moreover, a pressure regulating valve-inclusive waterproof cap 33 can be freely detachably attached to the electric connector 11 of the endoscope 2. The waterproof cap 33 has a pressure regulating cap that is not shown.

The outer surface of the endoscope 2 including the outer surfaces of the insertion member 7, control section 8, and linkage cord 9 are bared and can be sterilized while being exposed to high-temperature high-pressure steam. In short, the endoscope 2 withstands sterilization with high-temperature high-pressure steam.

A sterilization casing 34 in which the endoscope 2 is stowed is used to sterilize the endoscope 2 with high-temperature high-pressure steam.

The sterilization casing 34 consists of a tray 35 whose upper side is left open, and a lid member 36 that covers the open side of the tray 35.

The tray 35 and lid member 36 each have a plurality of air vent holes that is not shown. When a high-temperature high-pressure steam sterilizer is used to sterilize the endoscope with high-temperature high-pressure steam, steam permeates through the air vent holes.

The tray 35 has a stowage dent formed in conformity to the shape of the endoscope 2. The components of the endoscope 2 are settled at predetermined positions in the stowage dent. The stowage dent includes an insertion member restriction dent that is not shown. The elongated insertion member 7 that is flexible is stowed in the insertion member restriction dent.

Typical conditions for high-temperature high-pressure steam sterilization are stipulated in the standard ANSI/AAMI ST37-1992 recommended by the American National Standards Institute (ANSI) and published from the Association for the Advancement of Medical Instrumentation (AAMI). According to the standard, a pre-vacuum sterilization process should be performed at 132° C. for 4 min, and a gravity settling sterilization process should be performed at 132° C. for 10 min.

The condition of the temperature for sterilization with high-temperature high-pressure steam varies depending on the model of a high-temperature high-pressure steam sterilizer (or simply a sterilizer) or the time required for sterilization. Generally, the temperature ranges from about 115° C. to about 138° C.

Some sterilizers can be set to about 142° C. The condition of the time for sterilization varies depending on the condition of the temperature for sterilization. Generally, the time ranges from about 3 min to about 60 min. Some types of sterilizers can be set to about 100 min.

For the sterilization, the pressure in a sterilization chamber is made higher than the atmospheric pressure by about 0.2 MPa.

A typical pre-vacuum type high-temperature high-pressure steam sterilization process includes a pre-vacuum step and a sterilization step. At the pre-vacuum step, the sterilization chamber in which equipment to be sterilized is placed is decompressed in preparation for the sterilization step. At the sterilization step, high-temperature high-pressure steam is fed into the sterilization chamber in order to sterilize an endoscope. The pre-vacuum step is a step needed to make preparations for infiltrating steam into every part of the equipment to be sterilized. Decompression of the sterilization chamber allows high-temperature high-pressure steam to permeate the whole equipment to be sterilized. At the pre-vacuum step, the pressure in the sterilization chamber is made lower than the atmospheric pressure by a value ranging from about 0.07 Mpa to about 0.09 MPa.

Some sterilization processes include a dry step that succeeds the sterilization step and at which the sterilization chamber is decompressed again in order to dry the sterilized equipment to be sterilized. At the dry step, the sterilization chamber is decompressed in order to exhaust steam from the sterilization chamber and to thus facilitate drying of the equipment to be sterilized in the sterilization chamber. At the dry step, the pressure in the sterilization chamber is made lower than the atmospheric pressure by a value ranging from about 0.07 MPa to about 0.09 MPa.

For sterilizing the endoscope 2 with high-temperature high-pressure steam, the pressure regulating valve-inclusive waterproof cap 33 is attached to the electric connector 11. In this state, the pressure regulating valve, which is not shown, of the waterproof cap 33 is closed. The air vent hole is blocked with the waterproof cap 33. The interior of the endoscope 2 is sealed to be watertight and airtight.

When a sterilization process including the pre-vacuum step is adopted, the pressure in the sterilization chamber is lowered at the pre-vacuum step. Consequently, when a difference in pressure is created between the interior and exterior of the endoscope 2, that is, the external pressure of the endoscope 2 gets lower than the internal pressure thereof. Eventually, the pressure regulating valve opens. The interior of the endoscope 2 therefore communicates with the exterior thereof through the air vent hole. This prevents creation of a large difference in pressure between the interior of the endoscope 2 and the sterilization chamber. Thus, the endoscope 2 will not be broken due to a difference in pressure between the interior and exterior thereof.

At the sterilization step, the sterilization chamber is pressurized. When a difference in pressure is created between the interior and exterior of the endoscope 2, that is, the external pressure of the endoscope 2 gets higher than the internal pressure thereof, the pressure regulating valve closes. High-temperature high-pressure steam will therefore not actively invade into the endoscope 2 through the waterproof cap 33 and air vent hole.

However, high-temperature high-pressure steam gradually invades into the endoscope 2 through the sheathing of the flexible tube or O rings. The sheathing of the flexible tube is made of a high polymer material. The O rings are seal means included in joints formed in the housing of the endoscope 2, and made of a fluorocarbon rubber or silicon rubber.

Incidentally, incoming pressure that is the sum of pressure released during decompression performed at the pre-vacuum step and pressure applied at the sterilization step is externally applied to the housing of the endoscope 2.

When a sterilization process including a decompression step that succeeds the sterilization step is adopted, the pressure in the sterilization chamber is lowered at the decompression step. When a difference in pressure is created between the interior and exterior of the endoscope 2, that is, the external pressure of the endoscope 2 gets lower than the internal pressure thereof, the pressure regulating valve opens nearly at the same time. Consequently, the interior of the endoscope 2 communicates with the exterior thereof through the air vent hole. This prevents creation of a large difference in pressure between the interior of the endoscope 2 and the sterilization chamber. Thus, the endoscope 2 will not be broken due to a difference in pressure between the interior and exterior thereof.

When the decompression step is completed, the sterilization chamber is pressurized. Consequently, when a difference in pressure is created between the interior and exterior of the endoscope 2, that is, the external pressure of the endoscope 2 gets higher than the internal pressure thereof, the pressure regulating valve closes.

When all the steps of a high-pressure steam sterilization process are completed, incoming pressure equivalent to pressure released at the decompression step is externally applied to the housing of the endoscope 2.

The waterproof cap 33 is then detached from the electric connector 11. Consequently, the interior of the endoscope 2 communicates with the exterior thereof through the air vent hole. The internal pressure of the endoscope 2 becomes equal to the atmospheric pressure. Consequently, the endoscope 2 is unloaded from the pressure applied to the housing of the endoscope 2.

Figure 2:
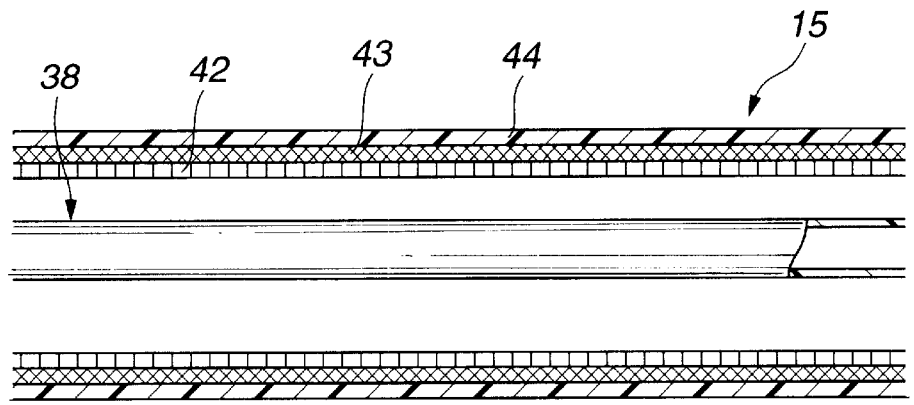

FIG. 2 is a longitudinal sectional view of the flexible tube 15.

The flexible tube 15 consists mainly of a spiral tube 42 that is the innermost layer, a braid 43, and a sheathing resin 44. The spiral tube 42 has a thin belt-like metallic piece spirally wound. The braid 43 mounted on the spiral tube 42 has metallic wires plaited. The sheathing resin 44 is coated over the periphery of the braid 43.

FIG. 2 shows only one spiral tube 42. Alternatively, the spiral tube 42 may be a two-ply or three-ply tube. The sheathing resin 44 is a resin material, for example, an ester-series thermoplastic elastomer, an amide-series thermoplastic elastomer, a styrene resin, a fluorocarbon rubber, or a silicon rubber. An elongated built-in component 38 that is flexible and realized with a hollow resin tube or the like shown in FIG. 3 is passed through the flexible tube 15 shown in FIG. 2.

Figure 3:
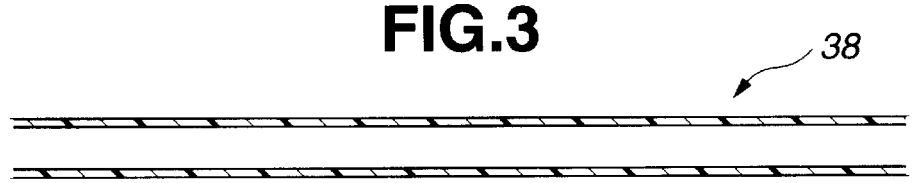

FIG. 3 is a longitudinal sectional view of the elongated built-in component 38.

The elongated built-in component 38 has the distal part connected to the distal part 17 with a metallic tube 37 (see FIG. 12A or FIG. 12B) or a base between them. The other end of the built-in component 38 is connected to a branching channel 41 (see FIG. 12A or FIG. 12B), which is incorporated in the endoscope 2, or a base in a space near the rear end of the insertion member. Thus, the built-in component 38 forms a channel.

For the elongated built-in component 38, a resin tube made of polytetrafluoroethylene (PTFE) is generally adopted. The elongated built-in component 38 may be, as shown in FIG. 3, a hollow channel through which fluid is sucked or a therapeutic instrument is passed. Otherwise, the elongated built-in component 38 may be a channel used to aerate or perfuse a body cavity or used for any other purpose.

Figure 4A:
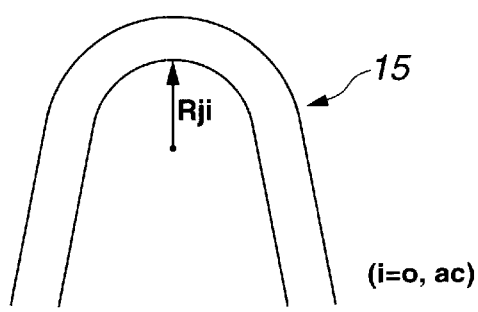
Figure 4B:
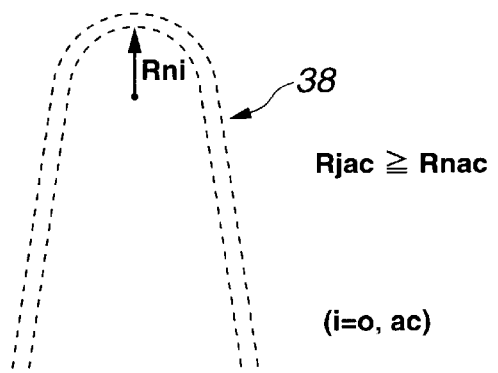

FIG. 4A and FIG. 4B are explanatory sectional views showing the flexible tube 15 whose critical radius of curvature is Rji (where i=o or ac) and the elongated built-in component 38 whose critical radius of curvature is Rni (where i=o or ac).

Herein, subscript i denotes a state. Hereinafter, a state attained before start of sterilization with high-temperature high-pressure steam, that is, a state in which the sterilization with high-temperature high-pressure steam has not been performed shall be a state o (i=o). A state attained after completion of the sterilization with high-temperature high-pressure steam shall be a state ac (i=ac). Accordingly, Rjo shall denote a critical radius of curvature the flexible tube 15 exhibits before the start of the sterilization with high-temperature high-pressure steam. Rjac shall denote a critical radius of curvature the flexible tube 15 exhibits after the completion of the sterilization with high-temperature high-pressure steam.

FIG. 4A shows the flexible tube 15 exhibiting a critical radius of curvature Rji. If the flexible tube 15 were bent to trace a circle whose radius is smaller than Rji, the flexible tube 15 would be buckled. Incidentally, the spiral tube 42, braid 43, and sheathing resin 44 described in conjunction with FIG. 2 are represented by one solid line in FIG. 4A.

FIG. 4B shows the elongated built-in component 38 that is passed through the flexible tube 15 and bent to trace a circle whose radius equals the critical radius of curvature Rni.

Herein, subscript i denotes a state. Hereinafter, a state attained before start of sterilization with high-temperature high-pressure steam, that is, a state in which sterilization with high-temperature high-pressure steam has not been performed shall be referred to as a state o (i=o). A state attained after completion of the sterilization with high-temperature high-pressure steam shall be referred to as a state ac (i=ac). Accordingly, Rno shall denote a critical radius of curvature the elongated built-in component 38 exhibits before the start of the sterilization with high-temperature high-pressure steam. Rnac shall denote a critical radius of curvature the elongated built-in component 38 exhibits after the completion of the sterilization with high-temperature high-pressure steam.

FIG. 4B shows the built-in component 38 exhibiting a critical radius of curvature Rni. If the built-in component 38 were bent to trace a circle whose radius is smaller than Rni, the built-in component 38 would be buckled. According to the first embodiment, the flexible tube 15 is structured to satisfy a condition of Rjo>Rjac. Moreover, the material of the flexible tube 15 and the material and thickness of a resin tube serving as the elongated built-in component 38 are determined so that the following conditional equation will be satisfied:

$$Rjac \geq Rnac$$

Next, an operation the present embodiment exerts will be described below.

As mentioned above, the condition of Rjo>Rjac is met. The critical radius of curvature the flexible tube 15 exhibits after completion of sterilization with high-temperature high-pressure steam is smaller than that the flexible tube 15 exhibits before the sterilization. In other words, after the completion of the sterilization with high-temperature high-pressure steam, the elongated built-in component 38 incorporated in the flexible tube 15 may be bent to trace a circle whose radius is smaller than that of a circle the built-in component 38 traces when bent before the start of the sterilization. However, since the condition of Rjac≧Rnac is met, even if the flexible tube 15 is bent to exhibit a radius of curvature equal to Rjac after the completion of the sterilization with high-temperature high-pressure steam, the elongated built-in component 38 will not buckle.

The present embodiment provides an advantage described below.

Even after completion of sterilization with high-temperature high-pressure steam, unless the flexible tube 15 of the insertion member 7 is bent to exhibit a radius of curvature equal to or smaller than the critical radius of curvature Rjac, the elongated built-in component 38 will not buckle. A feature the elongated built-in component 38 is requested to offer (insertion or removal of a therapeutic instrument, suction, aeration, perfusion, or the like) will not therefore be impaired.

Unless the flexible tube 15 is bent to exhibit a radius of curvature equal to or smaller than the critical radius of curvature Rjac, the endoscope that is so durable as to be used repeatedly for endoscopic examination can be provided.

(Second Embodiment)

A second embodiment of the present invention will be described below. The first embodiment has been described on the assumption that the flexible tube 15 is structured to satisfy the condition of Rjo>Rjac. The second embodiment will be described on the assumption that the flexible tube 15 is structured to satisfy the condition of Rjo≦Rjac.

According to the present embodiment, the flexible tube is structured to satisfy the condition of Rjo≦Rjac. Moreover, the flexible tube 15 and the elongated built-in component 38 are designed to satisfy the following condition:

$$Rjo \geq Rnac$$

The other components are identical to those of the first embodiment.

Next, an operation the present embodiment exerts will be described below.

Since the condition of Rjo≦Rjac is met, the critical radius of curvature the flexible tube 15 exhibits before start of sterilization with high-temperature high-pressure steam, that is, when sterilization with high-temperature high-pressure steam has not been performed is smaller than that the flexible tube 15 exhibits after completion of the sterilization. In other words, before the start of sterilization with high-temperature high-pressure steam, the elongated built-in component 38 incorporated in the flexible tube 15 may be bent to trace a circle whose radius is smaller than that of a circle the elongated built-in component 38 traces when bent after the completion of the sterilization.

On the other hand, the elongated built-in component 38 may satisfy Rno<Rnac or Rno=Rnac. Assuming that Rnac is made equal to or smaller than Rjo, even if the flexible tube 15 is bent to exhibit a radius of curvature equal to Rjo, the elongated built-in component 38 will not buckle irrespective of the time or temperature.

The present embodiment provides an advantage described below.

Unless the flexible tube 15 of the insertion member 7 is bent to exhibit a radius of curvature equal to or smaller than the critical radius of curvature Rjac the flexible tube exhibits after completion of sterilization with high-temperature high-pressure steam or the critical radius of curvature Rjo the flexible tube exhibits before start of the sterilization, the elongated built-in component 38 will not buckle. A feature the elongated built-in component 38 is requested to offer (insertion or removal of a therapeutic instrument, aeration, or perfusion) will not be impaired.

(Third Embodiment)

Next, a third embodiment of the present invention will be described below. The flexible tube 15 and elongated built-in component 38 are structured to meet the same condition as they are in the first embodiment (or the second embodiment) on the assumption that the temperature of the outer surface of the endoscope 2 attained after completion of sterilization with high-temperature high-pressure steam will be equal to or lower than approximately 40° C.

The temperature of approximately 40° C. is equal to or lower than the temperature at which denaturation occurs. Specifically, after the endoscope 2 is sterilized using a high-temperature high-pressure steam sterilizer, when the outer surface of the endoscope 2 is cooled to approximately 40° C., the endoscope 2 is reusable. When the insertion member 7 of the endoscope 2 is handled frequently, the possibility that the flexible tube 15 may be bent to exhibit a radius of curvature equal to Rjac gets higher.

Next, an operation the present embodiment exerts will be described below.

When the temperature of the outer surface of the endoscope 2 is equal to or lower than 40° C., if the flexible tube 15 were bent to exhibit a radius of curvature equal to Rjac (or Rjo), the elongated built-in component 38 would not buckle.

The present invention provides an advantage described below.

Even when the temperature of the outer surface of the endoscope 2 sterilized with high-temperature high-pressure steam is equal to or lower than 40° C., that is, the endoscope 2 is used for examination, the elongated built-in component 38 will not buckle. A feature the elongated built-in component 38 is requested to offer (insertion or removal of a therapeutic instrument, suction, aeration, or perfusion) will not therefore be impaired.

Incidentally, if the endoscope is transported from the high-temperature high-pressure steam sterilizer at the temperature of approximately 80° C., when the temperature of the outer surface of the endoscope is equal to or lower than approximately 80° C., the flexible tube and elongated built-in component incorporated in the endoscope may be structured to meet the same condition as they are in the first embodiment. In this case, whenever the endoscope 2 is used after sterilized with high-temperature high-pressure steam, the elongated built-in component 38 will not buckle.

(Fourth Embodiment)

Next, a fourth embodiment of the present invention will be described below. When a resin tube is used as the elongated built-in component 38, the hardness, thickness, and position of the resin tube and the clearance between the resin tube and the inner wall of the flexible tube 15 are determined as described below. Thus, the elongated built-in component 38 is prevented from being buckled or broken even when the flexible tube 15, in which all the elongated built-in components including the elongated built-in component 38 are incorporated, is bent to exhibit a radius of curvature equal to Rjac after completion of sterilization with high-temperature high-pressure steam.

The hardness of the resin tube is made much lower than the hardness of the flexible tube 15. Specifically, the hardness of the resin tube should preferably be confined to substantially 5% or less of the hardness of the flexible tube 15.

Next, the thickness of the resin tube will be described. When the resin tube is used as a suction channel that is also used to insert or remove a therapeutic instrument, the thickness generally ranges from about 0.4 mm to about 0.7 mm. A special resin tube whose thickness ranges from about 0.1 mm to about 0.4 mm may be adopted. When the resin tube is used as a channel dedicated to aeration or perfusion, the thickness of the resin tube ranges from about 0.2 mm to about 0.5 mm.

When the Rnac value is very close to the Rjac value (Rnac=approximately Rjac), the resin tube should preferably be located near the center axis of the flexible tube 15.

Figure 5:
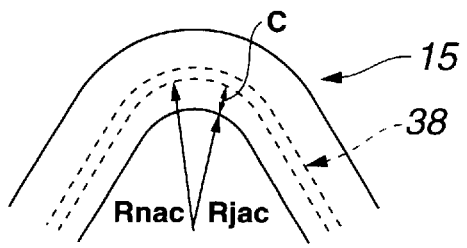
FIG. 5 is an explanatory diagram showing a bent flexible tube employed in a fourth embodiment.

As shown in FIG. 5, assuming that a distance (clearance) from the inner surface of the flexible tube 15 to the built-in component 38 realized with the resin tube is c, the resin tube should preferably be positioned so that the following relationship will be established:

$$Rnac \leq Rjac+c \text{ (where } c>0\text{)}$$

Next, an operation the present embodiment exerts will be described.

The hardness of the built-in component 38 realized with a resin tube is much lower than the hardness of the flexible tube 15. The resin tube is less likely to buckle than the flexible tube 15 is.

Moreover, the resin tube is positioned so that the relationship of Rnac≦Rjac+c (c>0) will be established. Even if the flexible tube 15 is bent to exhibit a radius of curvature equal to Rjac, the elongated built-in component 38 (resin tube) will not buckle. This is because the elongated built-in component 38 is bent to exhibit a radius of curvature corresponding to Rjac+c.

The present embodiment provides an advantage described below.

Since the resin tube does not buckle, a feature the resin tube is requested to offer (insertion or removal of a therapeutic instrument, suction, aeration, or perfusion) will not be impaired. Furthermore, the hardness of the resin tube is much lower than the hardness of the flexible tube 15, and will therefore hardly affect inserting smoothness.

(Fifth Embodiment)

Next, a fifth embodiment of the present invention will be described with reference to FIG. 6A to FIG. 7B.

In whatever situation or environment the endoscope 2 is placed, any time instant t before the endoscope 2 is first sterilized with high-temperature high-pressure steam shall be 0 (t=0). Herein, the situation or environment the endoscope may be placed is whether the endoscope 2 is currently used for examination or sterilized with high-temperature high-pressure steam, whether endoscopic examination or sterilization with high-temperature high-pressure steam has been started or has already been completed, or the like. The critical radius of curvature of the flexible tube 15 at a time instant t, which shall succeed the time instant 0 and correspond to the number of times by which sterilization with high-temperature high-pressure steam has been performed, shall be Rj(t). The critical radius of curvature of the elongated built-in component 38 at the time instant t shall be Rn(t). The elongated built-in component 38 is designed so that the following condition will be met:

$$Rj(t) \geq Rn(t)$$

Ten graphs of FIG. 6A to FIG. 6J are conceptual diagrams showing how the critical radius of curvature of the flexible tube 15 or elongated built-in component 38 changes with an increase in a time instant (with an increase in the number of times by which sterilization with high-temperature high-pressure steam is performed). The axis of abscissas indicates the time instant that is regarded as the number of times by which the endoscope 2 is sterilized with high-temperature high-pressure steam.

The axis of abscissas of FIG. 6B alone bears numerals, to show that the critical radius of curvature changes greatly after sterilization with high-temperature high-pressure steam has been performed once or twice. The other graphs merely express characteristic changes in critical radii of curvature. The axis of ordinates of each of the other graphs indicates the critical radius of curvature, but does not bear concrete numerals. Thus, each of the other graphs merely expresses a characteristic change in a critical radius of curvature.

FIG. 6A is a conceptual diagram showing a change in a critical radius of curvature occurring when the flexible tube 15 or elongated built-in component 38 deteriorates with the passage of time. FIG. 6B is a conceptual diagram showing a change in a critical radius of curvature occurring when the flexible tube 15 or elongated built-in component 38 does not deteriorate with the passage of time. In other words, the critical radius of curvature of the flexible tube 15 or elongated built-in component 38 decreases greatly in an early stage (after sterilization with high-temperature high-pressure steam has been performed once or twice). Thereafter, the critical radius of curvature hardly decreases.

FIG. 6C to FIG. 6F are concerned with the fifth embodiment. All the four graphs demonstrate that the critical radius of curvature Rj(t) of the flexible tube 15 is larger than the critical radius of curvature Rn(t) of the elongated built-in component 38 at any time instant. In short, Rj(t)>Rn(t) is met.

FIG. 6G to FIG. 6J are concerned with related arts in which the elongated built-in component 38 may buckle. All the four graphs of FIG. 6G to FIG. 6J demonstrate that when the flexible tube 15 is bent to exhibit a radius of curvature equal to Rj(a) at any time instant t=a, the elongated built-in component 38 buckles. Specifically, Rj(a)<Rn(a) is met at the time instant t=a, but the relationship of Rj(t)≧Rn(t) is not established thereat.

As mentioned above, the time instant t is associated with the number of times by which sterilization with high-temperature high-pressure steam has been performed. The foregoing relationship must be established within a short period of time that is a time interval from the start of an endoscopic examination through sterilization with high-temperature high-pressure steam to the start of the next endoscopic examination. This will be described in conjunction with FIG. 7A and FIG. 7B.

FIG. 7A shows an example of changes (transition) in the critical radii of curvature of the flexible tube 15 and elongated built-in component 38 occurring within a time interval from the start of an endoscopic examination through sterilization with high-temperature high-pressure steam to the start of the next endoscopic examination. The graph of FIG. 7B shows a change in the ambient temperature of the endoscope 2.

After an endoscopic examination is completed, when a pre-vacuum step preceding sterilization with high-temperature high-pressure steam is started, the ambient temperature of the endoscope 2 rises due to pre-heating, and the critical radii of curvature Rj(t) and Rn(t) of the flexible tube 15 and elongated built-in component 38 decrease.

Thereafter, when a sterilization step is started, the endoscope 2 is thermally loaded by a high-temperature high-pressure steam sterilizer. The critical radii of curvature of the flexible tube 15 and elongated built-in component 38 remain constantly low.

After the sterilization step is completed, a dry step is performed and preparations are made for an examination. The ambient temperature drops as time thus elapses until another examination is performed. The critical radii of curvature Rj(t) and Rn(t) of the flexible tube 15 and elongated built-in component 38 increase.

In FIG. 7A, the critical radii of curvature exhibited during the first examination are not different from those exhibited during the second examination. This is because these examinations are performed at any of time instants in FIG. 6B at which a time-passing deterioration hardly occurs. When the critical radii of curvature deteriorate with the passage of time, the critical radii of curvature exhibited during the first examination may be different from those exhibited during the second examination.

Next, an operation the present embodiment exerts will be described below.

At any time instant t, even if the flexible tube 15 is bent to exhibit a radius of curvature equal to Rj(t), the elongated built-in component 38 will not buckle.

The present embodiment provides an advantage described below.

At any time instant t, the elongated built-in component 38 does not buckle. Any feature the elongated built-in component 38 is requested to offer (insertion or removal of a therapeutic instrument, suction, aeration, or perfusion) will not be impaired.

Referring to FIG. 7A and FIG. 7B, as long as the insertion member 7 is not bent during sterilization with high-temperature high-pressure steam to such an extent that the flexible tube 15 or elongated built-in component 38 may buckle, Rj(t) may become smaller than Rn(t) during the sterilization.

(Sixth Embodiment)

Figure 8:
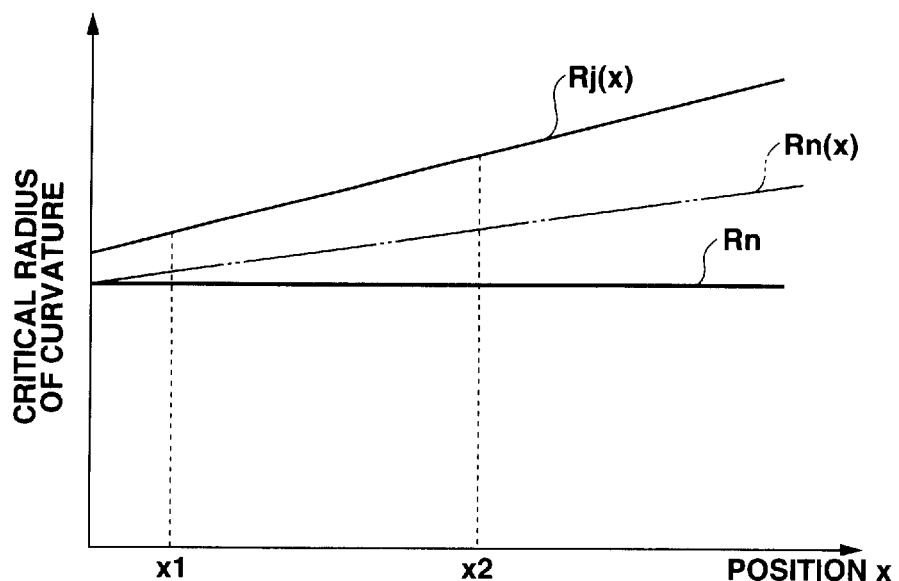
FIG. 8 shows the critical radii of curvature of a flexible tube and an elongated built-in component, which are employed in a sixth embodiment, in relation to a point in a longitudinal direction of the flexible tube.

Next, a sixth embodiment of the present invention will be described with reference to FIG. 8. FIG. 8 shows the critical radii of curvature of the flexible tube 15 and the elongated built-in component 38 in relation to a position in a longitudinal direction of the flexible tube 15 from the distal end thereof to the rear end thereof.

The critical radius of curvature of the flexible tube 15 varies depending on the position in the longitudinal direction. The critical radius of curvature of the elongated built-in component 38 remains unchanged irrespective of the position in the longitudinal direction. When the elongated built-in component 38 is incorporated in the flexible tube 15 for use, they are designed to meet the condition described below.

Assuming that a critical radius of curvature the flexible tube 15 exhibits at the position x in the longitudinal direction is Rj(x), the flexible tube 15 and the elongated built-in component 38 are combined so that the following condition may be met relative to any position x, $$Rj(x) \geq Rn$$

where Rn denotes the critical radius of curvature of the elongated built-in component 38. The critical radius of curvature Rn remains unchanged irrespective of the position x.

In general, the distal part of the flexible tube 15 of the endoscope 2 is structured to be softer than the proximal part thereof in consideration of inserting smoothness. In other words, the proximal part of the flexible tube 15 is harder than the distal part thereof.

The distal soft part of the flexible tube 15 exhibits a smaller critical radius of curvature than the proximal part thereof. For example, referring to FIG. 8, when x1<x2, Rj(x1)<Rj(x2).

The critical radius of curvature is determined with the diameter of the flexible tube 15 or the dimensions or specifications of or for the spiral tube 42, braid 43, and sheathing resin 44.

Next, an operation the present embodiment exerts will be described below.

Even if the flexible tube 15 is bent at any position x to exert a radius of curvature equal to Rj(x), the elongated built-in component 38 will not buckle.

The present invention provides an advantage described below.

The elongated built-in component 38 will not buckle at any position x. A feature the elongated built-in component 38 is requested to offer (insertion or removal of a therapeutic instrument, suction, aeration, or perfusion) will not be impaired.

Furthermore, when the flexible tube is bent to such as extent that the elongated built-in component 38 buckles, the flexible tube 15 will buckle. The user of the endoscope 2 can therefore recognize the failure readily.

(Seventh Embodiment)

Next, a seventh embodiment of the present invention will be described. The elongated built-in component 38 that exhibits a different critical radius of curvature depending on the position thereon in a longitudinal direction thereof is incorporated in the flexible tube 15 that exhibits a different critical radius of curvature depending the position thereon in a longitudinal direction. In this case, a critical radius of curvature the flexible tube 15 exhibits at the position x in the longitudinal direction shall be Rj(x), and a critical radius of curvature the elongated built-in component 38 exhibits at the position x in the longitudinal direction shall be Rn(x). The flexible tube 15 and the elongated built-in component 38 that is incorporated in the flexible tube 15 are designed to meet the following condition relative to any position x:

$Rj(x) \geq Rn(x)$

FIG. 8 shows an example of the critical radius of curvature Rn(x) with an alternate long and two short dashes line.

Next, an operation the present embodiment exerts will be described below.

Even if the flexible tube 15 is bent to exhibit a radius of curvature equal to Rj(x) at any position x, the elongated built-in component 38 will not buckle.

The present embodiment provides an advantage described below.

The elongated built-in component 38 will not buckle at any position x. A feature the elongated built-in component is requested to offer (insertion or removal of a therapeutic instrument, suction, aeration, or perfusion) will not be impaired.

(Eighth Embodiment)

Figure 9:
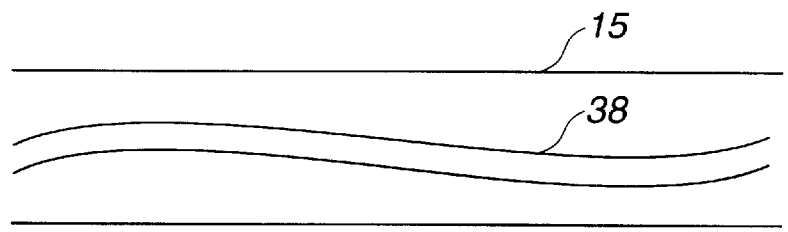
FIG. 9 shows a flexible tube employed in an eighth embodiment of the present invention and elongated built-in components passed through the flexible tube.

Next, an eighth embodiment of the present invention will be described in conjunction with FIG. 9. The elongated built-in component 38 is incorporated in the flexible tube 15 while having slack therein as shown in FIG. 9. Herein, the elongated built-in component 38 and flexible tube 15 are designed to meet the condition of Rjac≧Rnac after completion of sterilization with high-temperature high-pressure steam.

Next, an operation the present embodiment exerts will be described below.

After sterilization with high-temperature high-pressure steam is completed, the condition of Rjac≧Rnac is met. Therefore, even if the flexible tube 15 is bend to exhibit a radius of curvature equal to Rjac, the elongated built-in component 38 will not buckle. Furthermore, the elongated built-in component 38 is incorporated in the flexible tube 15 while having slack therein. Therefore, if the flexible tube 15 is bent to exhibit a radius of curvature equal to the critical radius of curvature Rjac, the slack in the elongated built-in component 38 disappears but the elongated built-in component 38 is not stretched tight.

The elongated built-in component 38 will therefore not buckle. Furthermore, the ends of the elongated built-in component 38 will not be burdened.

The present embodiment provides an advantage described below.

The elongated built-in component 38 will not buckle even after completion of sterilization with high-temperature high-pressure steam. Therefore, feature the elongated built-in component 38 is requested to offer (insertion or removal of a therapeutic instrument, aeration, or perfusion) will not be impaired. Furthermore, the ends of the elongated built-in component 38 will not be burdened. This leads to a decrease in the probability of occurrence of a defect such as a leakage of water derived from breakage of the ends.

(Ninth Embodiment)

Next, a ninth embodiment of the present invention will be described. The elongated built-in component 38 is incorporated in the flexible tube 15 while having slack therein. Herein, the elongated built-in component 38 and flexible tube 15 are designed to meet the condition of Rjac<Rnac after completion of sterilization with high-temperature high-pressure steam.

An operation the present embodiment exerts will be described below.

After completion of sterilization with high-temperature high-pressure steam, the condition of Rjac<Rnac is met. Therefore, unless the elongated built-in component 38 has slack therein, the elongated built-in component 38 will be readily buckled if the flexible tube 15 is bent to exhibit a radius of curvature equal to Rjac. However, after completion of sterilization with high-temperature high-pressure steam, the elongated built-in component 38 has slack therein while lying through the flexible tube 15. When the flexible tube 15 is bent, the slack in the elongated built-in component 38 is released. Thus, the elongated built-in component 38 is prevented from buckling. The same operation as the operation exerted when Rjac≧Rnac is met is apparently provided.

The present embodiment provides an advantage described below.

The elongated built-in component 38 will not buckle even after completion of sterilization with high-temperature high-pressure steam. Therefore, a feature the elongated built-in component 38 is requested to offer (insertion or removal of a therapeutic instrument, aeration, perfusion) will not be impaired.

(Tenth Embodiment)

Figure 10A:
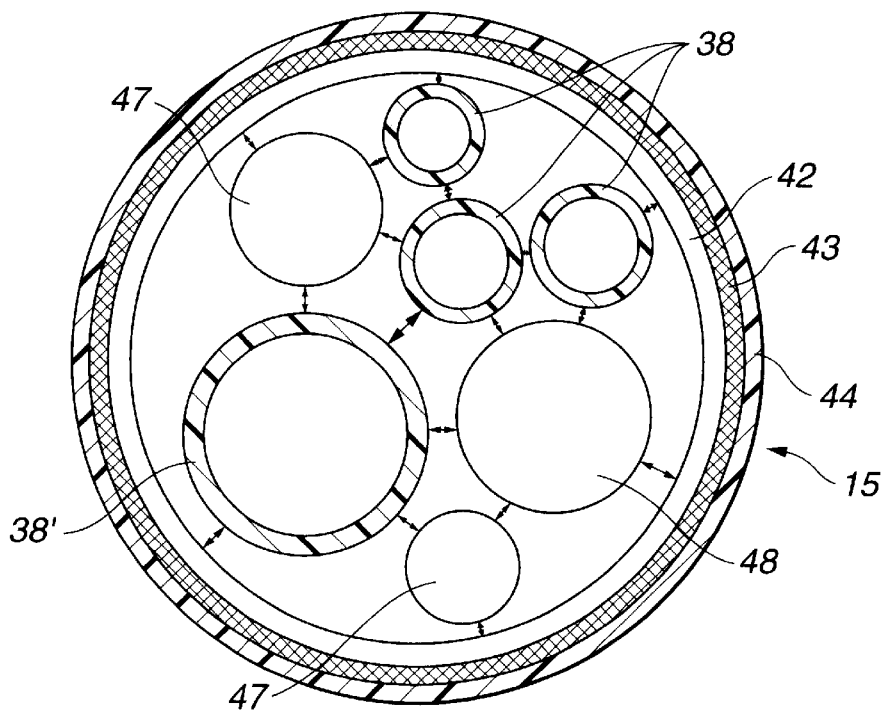
FIG. 10A and FIG. 10B are concerned with a tenth embodiment of the present invention.
Figure 10B:
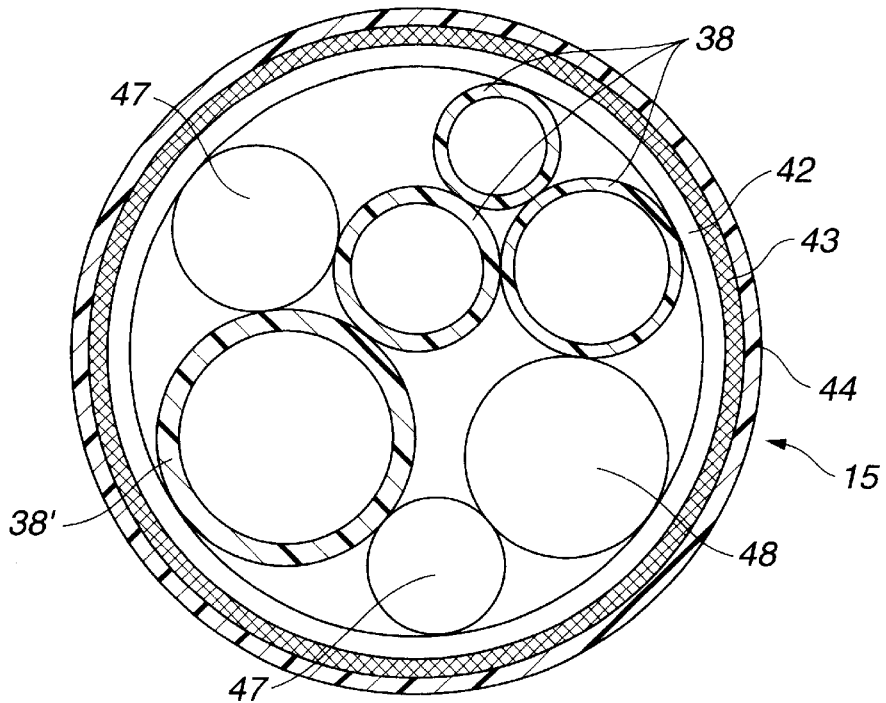

Next, a tenth embodiment of the present invention will be described below. FIG. 10A and FIG. 10B are explanatory cross-sectional views of the flexible tube 15 employed in the tenth embodiment.

FIG. 10A shows a case where the diameters of the elongated built-in components 38 are not larger before start of sterilization with high-temperature high-pressure steam or after completion of the sterilization, that is, the tenth embodiment. FIG. 10B shows a case where the diameters of the elongated built-in components 38 are larger after completion of sterilization with high-temperature high-pressure steam, that is, a related art that does not meet a condition met by the tenth embodiment.

FIG. 10A shows an example of a cross section of the insertion member 7. Elongated built-in components 38 and 38' having different diameters and illumination light propagation fiber bundles 47 are built in the flexible tube 15. The built-in component 38' that is hollowed and has a large cross-sectional area is a therapeutic instrument passage tube forming a therapeutic instrument channel. The built-in components 38 having smaller cross-sectional areas include an aeration tube and a perfusion tube.

As illustrated, clearances are preserved among the elongated built-in components 38, between each of the elongated built-in components 38 and each of the illumination light propagation fiber bundles 47 and an image transmission cable 48, and between each of the built-in components, illumination light propagation fiber bundles, and image transmission cable and the inner wall of the flexible tube 15, that is, the spiral tube 42. In FIG. 10A, bidirectional arrows indicate each clearance.

Referring to FIG. 10B, after completion of sterilization with high-temperature high-pressure steam, the clearances shown in FIG. 10A are unfound among the elongated built-in components 38, between each of the elongated built-in components and each of the illumination light propagation fiber bundles 47 and image transmission cable 48, and between each of the built-in components, illumination light propagation fiber bundles, and image transmission cable and the inner wall of the flexible tube 15, that is, the spiral tube 42.

This may be attributable to the fact that the outer diameters of the elongated built-in components 38 increase due to heat generated during sterilization with high-temperature high-pressure steam. Otherwise, the elongated built-in components 38 contract in longitudinal directions due to the heat generated during the sterilization with high-temperature high-pressure steam, whereby the outer diameters of the elongated built-in components 38 increase by the magnitudes of contraction. Otherwise, the sheathing resin 44 of the flexible tube 15 absorbs water to swell because of humidity raised during sterilization with high-temperature high-pressure steam. Consequently, the inner diameter of the flexible tube 15 itself decreases. Thus, the clearances are nullified because of the various factors.

The deformation nullifying the clearances may occur even after completion of one process of sterilization with high-temperature high-pressure steam or may occur due to repetition of the sterilization.

As mentioned above, the tenth embodiment includes the elongated built-in components 38 that have clearances among them and between each of them and each of the other built-in components.

Next, an operation the present embodiment exerts will be described below.

Even after completion of sterilization with high-temperature high-pressure steam, there are the clearances between each of the elongated built-in components 38 and each of the other built-in components or the inner wall of the flexible tube 15. Therefore, the elongated built-in components 38 can be moved in longitudinal directions while being kept apart from the other built-in components or the inner wall of the flexible tube 15. The elongated built-in components 38 will therefore neither extremely stretch nor slacken partly or as a whole.

The present embodiment provides an advantage described below.

Even after completion of sterilization with high-temperature high-pressure steam, the elongated built-in components 38 can be moved in longitudinal directions while being kept apart from the other built-in components and the inner surface of the flexible tube 15. Thus, even when the flexible tube 15 is bent, the elongated built-in components 38 will not buckle.

Since the elongated built-in components 38 will not buckle, features the elongated built-in components 38 are requested to offer (insertion or removal of a therapeutic instrument, aeration, and perfusion) will not be impaired. Furthermore, the ends of the elongated built-in components 38 will not be loaded. This leads to a decrease in the probability of occurrence of a defect such as a leakage of water derived from breakage of the ends.

Figure 11A:
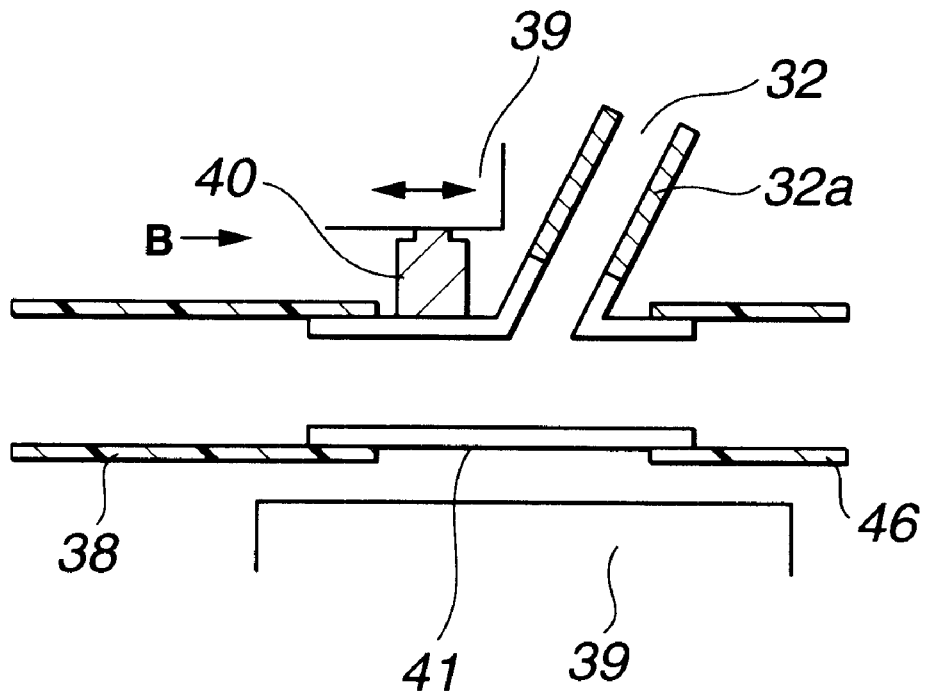
FIG. 11A is a longitudinal sectional view showing a rear part of a built-in component and its surroundings.

FIG. 11A shows a locking (holding) means for locking an end of a channel resin tube that serves as a built-in component 38 and forms a channel. The locking means locks (holds) the end of the resin tube to make the position in a longitudinal direction of the end adjustable. Specifically, the rear end of the channel resin tube is engaged with the front end of a branching channel 41. The front end of a tube 46 is engaged with the rear end of one of the branches of the branching channel 41. The other branch of the branching channel 41 is joined to an insertion port linkage channel 32a that opens on a therapeutic instrument insertion port 32.

Figure 11B:
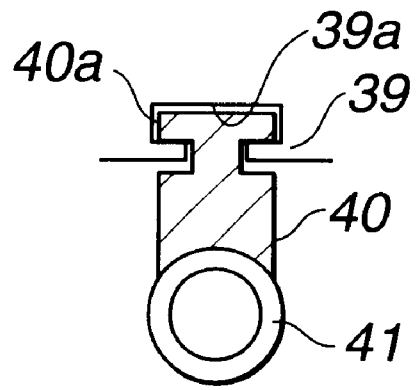
FIG. 11B shows the cross sections of the surroundings shown in FIG. 11A in a direction of arrow B shown in FIG. 11A.

Moreover, the branching channel 41 is held by a linkage tube 39 with a linkage member 40 between them. The linkage member 40 has, as shown in FIG. 11B that shows the cross sections of the members shown in FIG. 11A in a direction of arrow B, a rail 40a thereof fitted in a groove 39a formed along longitudinal directions (lateral directions in FIG. 11A) of the linkage tube 39. The linkage member 40 is held by the linkage tube 39 while being freely movable in the longitudinal directions.

As the locking means for locking one end of the resin tube serving as the built-in component 38, the branching channel 41 is held so that it can slide in the longitudinal directions of the control section 8. Consequently, if the resin tube should contract due to heat, the branching channel 41 will slide to prevent the resin tube from being stretched.

The above description has been made on the assumption that a channel serves as the built-in component. However, the built-in component is not necessary to be a channel. It can be a tube used to aerate or perfuse a body cavity. Moreover, a member capable of sliding need not be the branching channel 41. Anyhow, the member should merely be movable in longitudinal directions.

FIG. 12A and FIG. 12B are longitudinal sectional views of the insertion member 7. FIG. 12A shows a state of the insertion member 7 attained before start of sterilization with high-temperature high-pressure steam. FIG. 12B shows a state thereof attained after completion of the sterilization. A metallic tube 37 is fixed to the distal part 17. The flexible tube 15 is connected to the distal part 17 with the bending section 16 between them. An elongated built-in component 38 is fixed to the metallic tube 37, and passed through the flexible tube 15. The linkage tube 39 is fixed to the opposite end of the flexible tube 15. The branching channel 41 is fixed to the linkage tube 39 with the linkage member 40 between them.

One end of a bellows member 45 capable of stretching or contracting is fixed to the branching channel 41, and the other end is fixed to the elongated built-in component 38. Furthermore, the therapeutic instrument insertion port 32 and the tube 46 led to the control section 8 are fixed to the branching channel 41.

As mentioned above, the elongated built-in component 38 is indirectly fixed to the flexible tube 15. Needless to say, in addition to the illustrated therapeutic instrument passage channel, a channel used to aerate or perfuse a body cavity or any other channel used for any other purpose may serve as the elongated built-in component 38.

Referring to FIG. 12A and FIG. 12B, the bellows member 45 is used to link the elongated built-in component 38 and branching channel 41. The bellows member 45 may be used to link the elongated built-in component 38 and metallic tube 37. The bellows member 45 may be used in the both places.

An operation to be exerted will be described below.

When the elongated built-in component 38 contracts after completion of sterilization with high-temperature high-pressure steam, the bellows member 45 stretches. Furthermore, when the flexible tube 15 is bent to exhibit a radius of curvature equal to the critical radius of curvature Rjac, the bellows member 45 stretches. Therefore, the elongated built-in component 38 will not buckle.

The present structure provides an advantage described below.

Even after completion of sterilization with high-temperature high-pressure steam, the elongated built-in component 38 will not buckle. Therefore, the features the elongated built-in component 38 is requested to offer (insertion or removal of a therapeutic instrument, aeration, or perfusion) will not be impaired. In the structure shown in FIG. 12A and FIG. 12B, the bellows member 45 and elongated built-in component 38 may be molded in one united body. In this case, bellows serving as the bellows member 45 may be molded near the branching channel 41 or near the metallic tube 37, or in the middle between the branching channel 41 and the metallic tube 37.

In this case, an advantage described below is provided.

In addition to the advantage provided by the structure shown in FIG. 12A and FIG. 12B, since the bellows are molded as an integral part of the elongated built-in component 38, the labor for assembling components is saved. This is cost-effective. Moreover, there is no physical joint between the bellows member 45 and elongated built-in component 38. Consequently, the probability of occurrence of a defect such as a leakage of water decreases.

What is claimed is:

1. An endoscope having a soft insertion member that includes a flexible tube in which an elongated flexible built-in component is incorporated, and withstanding sterilization with high-temperature high-pressure steam during which an endoscope is sterilized while being exposed to high-temperature high-pressure steam, wherein:

a critical radius of curvature said elongated built-in component exhibits after completion of sterilization with high-temperature high-pressure steam, Rn, is equal to or smaller than a critical radius of curvature said flexible tube exhibits after the sterilization, Rj; that is, the following condition is met:

$Rn \leq Rj$ after completion of sterilization with high-temperature high-pressure steam, if said elongated built-in component is bent to exhibit a radius of curvature equal to or smaller than the critical radius of curvature Rn, said elongated built-in component is buckled; and after completion of the sterilization, if said flexible tube is bent to exhibit a radius of curvature equal to or smaller than the critical radius of curvature Rj, said flexible tube is buckled.

2. An endoscope according to claim 1, wherein: the critical radius of curvature said elongated built-in component exhibits after sterilization with high-temperature high-pressure steam, Rn, is equal to or smaller than a critical radius of curvature said flexible tube exhibits before start of the sterilization, Rj', and the critical radius of curvature said flexible tube exhibits after the sterilization, Rj; that is, the following condition is met:

$Rn \leq Rj$ and $Rn \leq Rj'$.

3. An endoscope according to claim 1, wherein: the critical radius of curvature said flexible tube exhibits after completion of sterilization with high-temperature high-pressure steam, Rj, is equal to or smaller than the critical radius of curvature said flexible tube exhibits before start of the sterilization, Rj'; that is, the following condition is met:

$Rj' \leq Rj$.

4. An endoscope according to claim 1, wherein after completion of sterilization with high-temperature high-pressure steam, said elongated built-in component has slack therein relative to said flexible tube.

5. An endoscope according to claim 1, wherein when the critical radius of curvature of said flexible tube varies depending on a portion of said flexible tube that extends in a longitudinal direction of said insertion member, the critical radius of curvature of said elongated built-in component is equal to or smaller than a critical radius of curvature any portion of said flexible tube exhibits.

6. An endoscope according to claim 5, wherein the critical radius of curvature of said elongated built-in component varies depending on a portion of said elongated built-in component that extends in the longitudinal direction of said insertion member.

7. An endoscope according to claim 5, wherein a critical radius of curvature the distal portion of said flexible tube, which is distal in the longitudinal direction, exhibits is smaller than a critical radius of curvature the proximal portion thereof exhibits.

8. An endoscope according to claim 5, wherein a critical radius of curvature the distal portion of said elongated built-in component, which is distal in the longitudinal direction, exhibits is smaller than a critical radius of curvature the proximal portion thereof exhibits.

9. An endoscope according to claim 1, wherein said elongated built-in component is realized with a hollow tube.

10. An endoscope according to claim 9, wherein said hollow tube is a resin tube made of a resin.

11. An endoscope according to claim 9, wherein said hollow tube is a tube dedicated to passage of a therapeutic instrument, suction, aeration, or perfusion.

12. An endoscope according to claim 1, wherein: even after completion of sterilization with high-temperature high-pressure steam, there are clearances between said elongated built-in component and the inner wall of said flexible tube, and between said elongated built-in component and each of the other built-in components; and said elongated built-in component is movable in the longitudinal directions of said insertion member.

13. An endoscope according to claim 1, wherein even after sterilization with high-temperature high-pressure steam is repeatedly performed, the critical radius of curvature of said elongated built-in component, Rn, is equal to or smaller than the critical radius of curvature of said flexible tube, Rj; that is, the following condition is met:

$Rn \leq Rj$.

14. An endoscope comprising:

an insertion member including a flexible tube that has a critical radius of curvature of buckling;

a hollow channel rearranged in the insertion member, the hollow channel having a critical radius of curvature of buckling, the critical radius of curvature of the hollow channel after completion of sterilization of the endoscope with high-temperature high-pressure steam is equal to or smaller than the critical radius of curvature of the flexible tube after completion of the sterilization.

15. The endoscope as claimed in claim 14, wherein the critical radius curvature of the flexible tube changes before and after the sterilization.

16. The endoscope as claimed in claim 15, wherein the critical radius of curvature of the flexible tube before start of the sterilization is greater than the critical radius of curvature of the flexible tube after the completion of the sterilization, the critical radius of curvature of the hollow channel after completion of the sterilization is equal to or smaller than that of the flexible tube after the completion of the sterilization.

17. The endoscope as claimed in claim 15, wherein the critical radius of curvature of the flexible tube before start of the sterilization is smaller than the critical radius of curvature of the flexible tube after the completion of the sterilization, the critical radius of curvature of the hollow channel after completion of the sterilization is equal to or smaller than that of the flexible tube before the start of the sterilization.

18. The endoscope as claimed in claim 14, wherein the critical radius of curvature of the flexible tube after the sterilization is the same as that of the flexible tube before sterilization.

19. The endoscope as claimed in claim 18, wherein than the critical radius of curvature of the hollow channel after the completion of the sterilization is equal to or smaller than that of the flexible tube after the completion of the sterilization.

20. The endoscope as claimed in claim 14, wherein the hollow channel incorporated in the flexible tube has slack therein relative to the flexible tube after the completion of the sterilization.

21. The endoscope as claimed in claim 14, wherein the critical radius of curvature of the flexible tube varies depending on a portion thereof in a longitudinal direction of the insertion member, the critical radius of curvature of the hollow channel is equal to or smaller than the critical radius of curvature at any portion of the flexible tube.

22. The endoscope as claimed in claim 21, wherein the critical radius of curvature of the hollow channel varies depending on a portion thereof in the longitudinal direction of the insertion number.

23. The endoscope as claimed in claim 22, wherein the insertion member further includes a bending section located distally to the flexible tube and a distal part located distally to the bending section, and wherein the critical radius of curvature at a distal portion of the flexible tube in a longitudinal direction of the flexible tube is smaller than the critical radius of curvature at a proximal portion thereof.

24. The endoscope as claimed in claim 23, wherein the critical radius of curvature at a distal portion of the hollow channel in a longitudinal direction of the hollow channel is smaller than the critical radius of curvature at a proximal portion thereof.

25. The endoscope as claimed in claim 14, wherein the hollow channel is made of a resin.

26. The endoscope as claimed in claim 14, wherein the hollow channel is arranged in the insertion member so that clearances are provided between the hollow channel, and inner wall of the flexible tube, and built-in components incorporated in the insertion member, and that the hollow channel is movable in a longitudinal direction of the insertion member.

27. The endoscope as claimed in claim 14, wherein the critical radius of curvature of the hollow channel after repeatedly performed the sterilization with high-temperature high-pressure steam is equal to or smaller than the critical radius of curvature of the flexible tube.

* * * * *